(12) United States Patent
Shvetsov et al.

(10) Patent No.: US 8,641,488 B1
(45) Date of Patent: Feb. 4, 2014

(54) INTAKE APPARATUS AND SYSTEM

(75) Inventors: Kyrylo Shvetsov, Tonowanda, NY (US); Anthony Lizauckas, III, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 685 days.

(21) Appl. No.: 12/818,777

(22) Filed: Jun. 18, 2010

Related U.S. Application Data

(60) Provisional application No. 61/218,274, filed on Jun. 18, 2009.

(51) Int. Cl.
*F24F 7/04* (2006.01)
*F24F 7/00* (2006.01)

(52) U.S. Cl.
USPC ............... 454/63; 454/49; 604/313; 604/314; 604/316; 604/289; 604/290; 604/294; 604/295; 604/296; 606/4; 606/5; 606/6; 606/162

(58) Field of Classification Search
USPC ....................... 454/63, 49; 604/313, 315, 316, 604/289–291, 294–296; 606/4–6, 107, 606/161–162, 166
See application file for complete search history.

(56) References Cited

U.S. PATENT DOCUMENTS

| | | | | |
|---|---|---|---|---|
| 4,880,352 A * | 11/1989 | Aarestad | ..................... | 415/182.1 |
| 5,015,243 A * | 5/1991 | Schifano | ....................... | 604/315 |
| 5,055,100 A * | 10/1991 | Olsen | .............................. | 604/22 |
| 5,156,618 A * | 10/1992 | Fiore et al. | .................... | 604/315 |
| 5,199,944 A * | 4/1993 | Cosmescu | ....................... | 604/26 |
| 5,328,152 A * | 7/1994 | Castle | ........................... | 251/229 |
| 5,971,977 A * | 10/1999 | Korenfeld | ........................ | 606/1 |
| 6,126,668 A * | 10/2000 | Bair et al. | ...................... | 606/166 |
| 6,146,353 A * | 11/2000 | Platt, Jr. | .......................... | 604/22 |
| 6,267,752 B1 * | 7/2001 | Svetliza | ........................ | 604/294 |
| 6,326,590 B1 * | 12/2001 | Shaffer et al. | ............. | 219/121.84 |
| 6,344,040 B1 * | 2/2002 | Juhasz et al. | ...................... | 606/4 |
| 6,440,109 B1 * | 8/2002 | Mastel | .......................... | 604/313 |
| 6,752,778 B1 * | 6/2004 | Fiedler et al. | ................... | 604/23 |
| 7,018,376 B2 * | 3/2006 | Webb et al. | ........................ | 606/4 |
| 7,762,965 B2 * | 7/2010 | Slatkine | ........................... | 601/7 |
| 2001/0021844 A1 * | 9/2001 | Kurtz et al. | ...................... | 606/5 |
| 2007/0083221 A1 * | 4/2007 | Carda | .......................... | 606/166 |
| 2007/0093795 A1 * | 4/2007 | Melcher et al. | ................. | 606/10 |
| 2007/0173791 A1 * | 7/2007 | Raksi | .................................. | 606/4 |
| 2008/0103367 A1 * | 5/2008 | Burba et al. | .................. | 600/236 |
| 2009/0118587 A1 * | 5/2009 | Voegele et al. | ............... | 600/206 |
| 2009/0149857 A1 * | 6/2009 | Culbert et al. | .................. | 606/80 |

* cited by examiner

*Primary Examiner* — Kang Hu
*Assistant Examiner* — Nathaniel Herzfeld
(74) *Attorney, Agent, or Firm* — Phillips Lytle LLP

(57) ABSTRACT

A smoke capture adapter comprising: a first adapter part having a first generally ring-shaped portion with a first cylindrical inner surface for securely engaging a laser apparatus having a beam propagation axis, the first generally ring-shaped portion being oriented such that the beam propagation axis passes through a region bound the first generally ring-shaped portion and a tubular outlet extending from said first generally ring-shaped portion for communicating with a vacuum tube; a second adapter part rotatably connected to the first adapter part and arranged to rotate generally about the beam propagation axis having a second generally ring-shaped portion adjacent the first generally ring-shaped portion, the first and second generally ring-shaped portions defining a generally toroidal cavity and an inlet in fluid communication with the cavity; the tubular outlet and inlet in fluid communication through the cavity; whereby the position of the inlet relative to the first adapter part may be adjusted by rotating the second adapter part relative to the first adapter part.

12 Claims, 8 Drawing Sheets

INTAKE APPARATUS AND SYSTEM

CROSS-REFERENCE TO RELATED APPLICATIONS

This application claims the benefit of U.S. Provisional Patent Application No. 61/218,274, filed Jun. 18, 2009. The entire content of such application is incorporated by reference herein.

TECHNICAL FIELD

The present invention relates generally to smoke evacuation and, more specifically, to an improved apparatus and system for smoke evacuation during medical procedures which use laser equipment, or where such equipment is present.

BACKGROUND

Lasers used in medical procedures include Carbon Dioxide and Er:Yag type lasers. Each uses different physics behind skin vaporization: Carbon Dioxide relies on a thermomechanical reaction that destroys dermal vessels and denaturates dermal proteins, and Er:Yag uses a photomechanical reaction to eject desiccated tissue from its location at a supersonic speed. Both procedures potentially release harmful contaminants. A discussion of laser resurfacing may be found in Robert S. Bader, MD, Cutaneous Laser Resurfacing, Carbon Dioxide, emedicine, Nov. 13, 2007, found at emedicine.medscape.com/article/1120283-overview, incorporated herein by reference, and Meir Cohen, MD, MPS and Marvin Spann, MD, Skin Resurfacing, Erbium YAG Laser, emedicine, Feb. 16, 2009, found at emedicine.medscape.com/article/1296908-overview, incorporated herein by reference.

BRIEF SUMMARY OF THE INVENTION

With parenthetical reference to the corresponding parts, portions, or surfaces of the disclosed embodiment, merely for purposes of illustration and not by way of limitation, the present invention broadly provides a first embodiment (60) of a smoke capture adapter comprising: a first adapter part (10) having a first generally ring-shaped portion (17) with a first cylindrical inner surface (12) for securely engaging a laser apparatus (30) having a beam propagation axis (91). In one aspect, the first generally ring-shaped portion (17) is oriented such that the beam propagation axis (91) passes through a region bound by the first generally ring-shaped portion (17). In another aspect, the adapter includes a tubular outlet (11) extending from the first generally ring-shaped portion (17) arranged for communication with a vacuum tube. In yet another aspect, the adapter comprises: a second adapter part (20) rotatably connected to the first adapter part (10) and arranged to rotate generally about the beam propagation axis (91), the second adapter part (20) having a second generally ring-shaped portion (27) adjacent the first generally ring-shaped portion (17), said first and second generally ring-shaped portions (17,27) defining a generally toroidal cavity (25). One aspect of the invention includes an inlet (21) in fluid communication with the toroidal cavity (25), wherein the tubular outlet (11) and the inlet (21) may be in fluid communication through the toroidal cavity (25). In certain aspects, the position of the inlet (21) relative to the first adapter part (10) may be adjusted by rotating the second adapter part (20) relative to the first adapter part (10). In other aspects, the inlet (21) may be directed away from the generally toroidal cavity (25) and towards the beam propagation axis (91). The first cylindrical inner surface (12) may be configured to compressively engage an associated laser apparatus (30). Such a laser apparatus (30) may have an outer cylindrical surface of a lens body, and the first cylindrical inner surface may be configured to compressively engage this outer cylindrical surface. The second adapter part (20) may be configured and arranged to rotate 360 degrees relative the first adapter part (10). In another aspect, the inlet (121) may be telescopic (129). The second adapter part (20) may also have finger grips (23) on an outer circumference of the second adapter part (20). The adapter may also contain a clip (18) on said tubular outlet (11) configured for connection to the laser apparatus (30). The inlet (21) may taper outwardly from the generally toroidal cavity (25).

Another embodiment includes a generally semi-cylindrical portion (219) having a central cylinder axis (291) and a bottom surface (224) generally defining a plane (293) perpendicular to the central cylinder axis (291), the generally semi-cylindrical portion (219) configured and arranged to compressively engage a laser apparatus (30). In another aspect, the adapter includes an inlet portion (221) attached to the generally semi-cylindrical portion (219) and extending outwardly from the plane (293), the inlet (221) oriented to generally face the central cylinder axis (91), and a hollow body portion (216) in fluid communication with the inlet portion (221), the hollow body portion (216) adjacent to the generally semi-cylindrical portion (219). The hollow body portion (216) may comprise a tubular outlet (211) extending away from the central axis (291) and extending outwardly from the plane (293) in a direction generally opposite said inlet portion (221). This embodiment may further have a laser apparatus (30). The hollow body portion (216) may be attached to an exterior surface of the generally semi-cylindrical portion (219) and may reside generally outside the circumference of the generally semi-cylindrical portion. The laser apparatus (30) may have an outer cylindrical surface of a lens body, and the semi-cylindrical portion (219) may be configured to compressively engage the outer cylindrical surface. The inlet (221) may be telescopic. The adapter may contain a clip (218) on the tubular outlet (211) for connecting to the laser apparatus (30). The inlet (221) may taper outwards from the plane (293). The inlet (221) may have an end which is substantially flush with the inner surface (212) of the semi-cylindrical portion (219).

In another aspect, the invention provides a smoke capture adapter (60, 70, 80, 90) for use with a laser apparatus (30) having a laser propagation path (91, 291) comprising: an inlet (21, 221) configured for orientation towards the laser propagation path (91, 291); a tubular outlet (11, 211) in fluid communication with the inlet (21, 221) and oriented away from the laser propagation path (91, 291); compressive attachment means (17, 18, 218, 219) for connecting the smoke capture adapter (60, 70, 80, 90) to the laser apparatus (30); and adjustment means (17, 27, 129, 219) for adjusting the position of the inlet about the laser propagation path (91, 291). The adjustment means (17, 27, 129, 219) may comprise a joint configured to rotate generally about the laser propagation path (91, 291). The compressive attachment means (17, 19, 218, 219) may comprise a convex semi-cylindrical surface (212) configured to compressively engage a cylindrical surface of the laser apparatus (30). The inlet (121) may be telescopic (129).

In one aspect, a ring-shaped portion (17) may be configured and adapted for simple, releasable attachment to a laser lens. In another aspect, a half-ring or semicircular portion (219) is configured and adapted for simple, releasable attachment to a laser lens. The intake portion (21, 121, 221) may extend generally downwardly from the ring-shaped portion (17), or the half-ring or semicircular portion (219), and an exhaust, evacuation, or output portion (11, 211) may extend generally upwardly. The intake (21, 121, 221) and output portions (11, 211) allow for air and fluid communication or transmission from the target surface (43) to an output (such as a smoke evacuation device).

In another aspect, a smoke evacuator intake (60, 70, 80, 90) is mounted directly onto the last lens in a laser system (30). This configuration eliminates the need for smoke evacuator intake (21, 121, 221) to be mounted on a separate fixture or to be held by assisting staff close to the laser itself. This in turn reduces and/or eliminates the need for the doctor to give constant command on the proper positioning of the intake.

In another aspect, a smoke evacuation nozzle may be positioned, for example, 0.5-2 inches below the lens of the laser allowing for the smoke capture to take place before it reaches the lens and low enough before the cross section area of the smoke cone becomes too wide to capture.

In another aspect of the invention, in addition to mounting to the lens, a smoke capture intake (21, 121, 221) is positioned below the level of the lens and is directed at the smoke site. This intake (21, 121, 221) may be movable or stationary. In the case of a movable intake, the intake (21, 121) may optionally be turned 360 degrees around the laser, which allows for the nozzle to be hidden behind the laser and not be seen by the doctor performing the procedure.

In another aspect of the invention, the intake apparatus (60, 70, 80, 90) is connected to a hose which in turn is connected to a medical smoke evacuator. Medical smoke evacuators may be used to extract living organisms (e.g. microbes, bacteria, etc) from the air with the use of Medical Filters (ULPA classification), thus preventing medical staff from inhaling potentially dangerous matter.

PREFERRED EMBODIMENTS OF THE INVENTION

Figure 1:
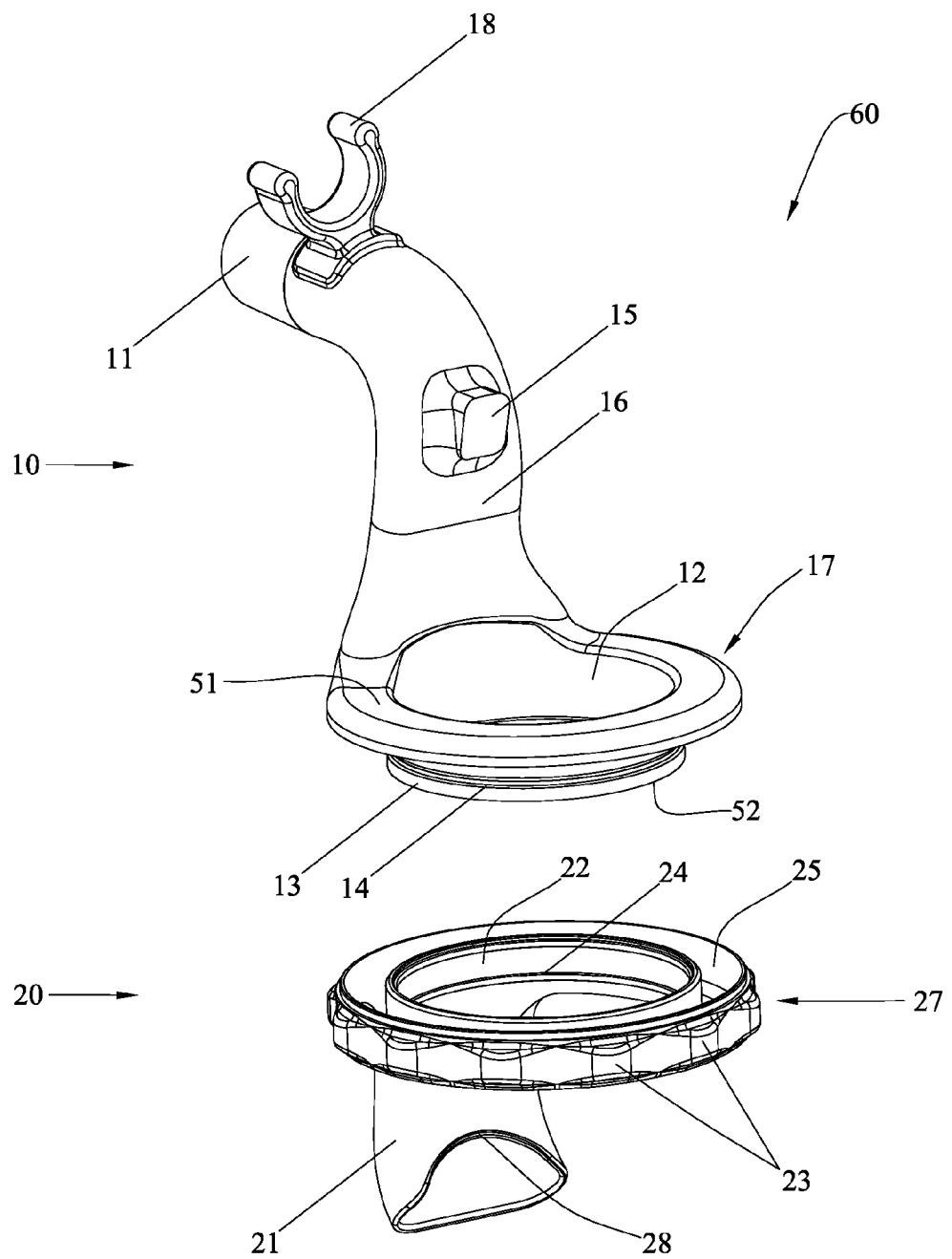
FIG. 1 is an exploded isometric view of a first embodiment.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Figure 5:
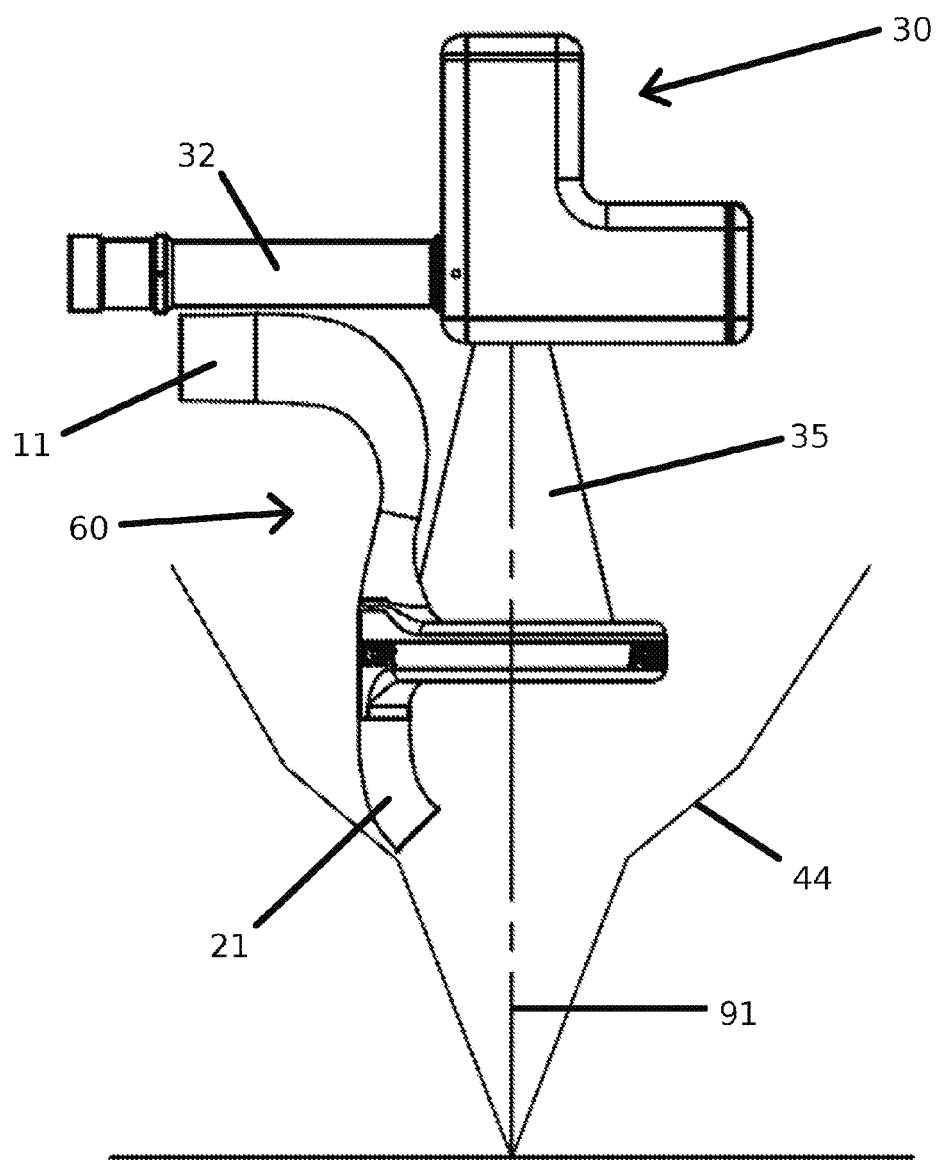
FIG. 5 is a side view of the first embodiment attached to a laser apparatus.

Referring now to the drawings, and more particularly, to FIG. 1 thereof, a first embodiment of a smoke capture adapter 60 is shown. As shown in FIG. 5, embodiment 60 is configured to attach to laser apparatus 30 such as a Sciton Laser attachment or similar device. Referring to FIG. 1, embodiment 60 is generally comprised of first adapter part 10 and second adapter part 20. First part 10 has a horizontally extending tubular outlet 11 which is configured to connect to a vacuum hose. As shown in FIG. 5, when embodiment 60 is attached to laser apparatus 30, tubular outlet 11 may extend parallel to tubular portion 32 of laser apparatus 30. Clip 18, shown in FIG. 1, is optionally mounted along the tubular body of outlet 11, which is configured for compressive attachment to tubular portion 32.

As shown in FIG. 1, tubular outlet 11 is generally horizontal and communicates and makes contact with hollow body portion 16. Hollow body portion 16 is generally vertical tube-like and has a rectangular extrusion 15 extending from its outer surface. Hollow body portion 16 connects tubular outlet 11 with first generally ring-shaped portion 17. First generally ring-shaped portion 17 has disk-shaped upper horizontal surface 51 connected to vertical inner cylindrical surface 12. Inner surface 12 is configured to compressively engage an outer cylindrical surface of laser apparatus 30. Inner surface 12 extends downwardly to disk-shaped lower horizontal surface 52, which connects to outer vertical cylindrical surface 13. In this embodiment, outer vertical cylindrical surface 13 has ridge 14 centered along its circumference.

Cylindrical surface 13 is configured to be extended into second generally ring-shaped portion 27 of second adapter part 20. Second generally ring-shaped portion 27 has an inner cylindrical surface 22 which has ridge 24 along its inner circumference. The sizes of cylindrical surface 13, inner surface 22, and ridges 14 and 24 are configured to allow parts 10 and 20 to snap together and, in certain embodiments, to form an air-tight seal. When ring-shaped portions 17 and 27 are brought together as described and shown in FIG. 2, a generally toroidal cavity 25 is formed.

Figure 2:
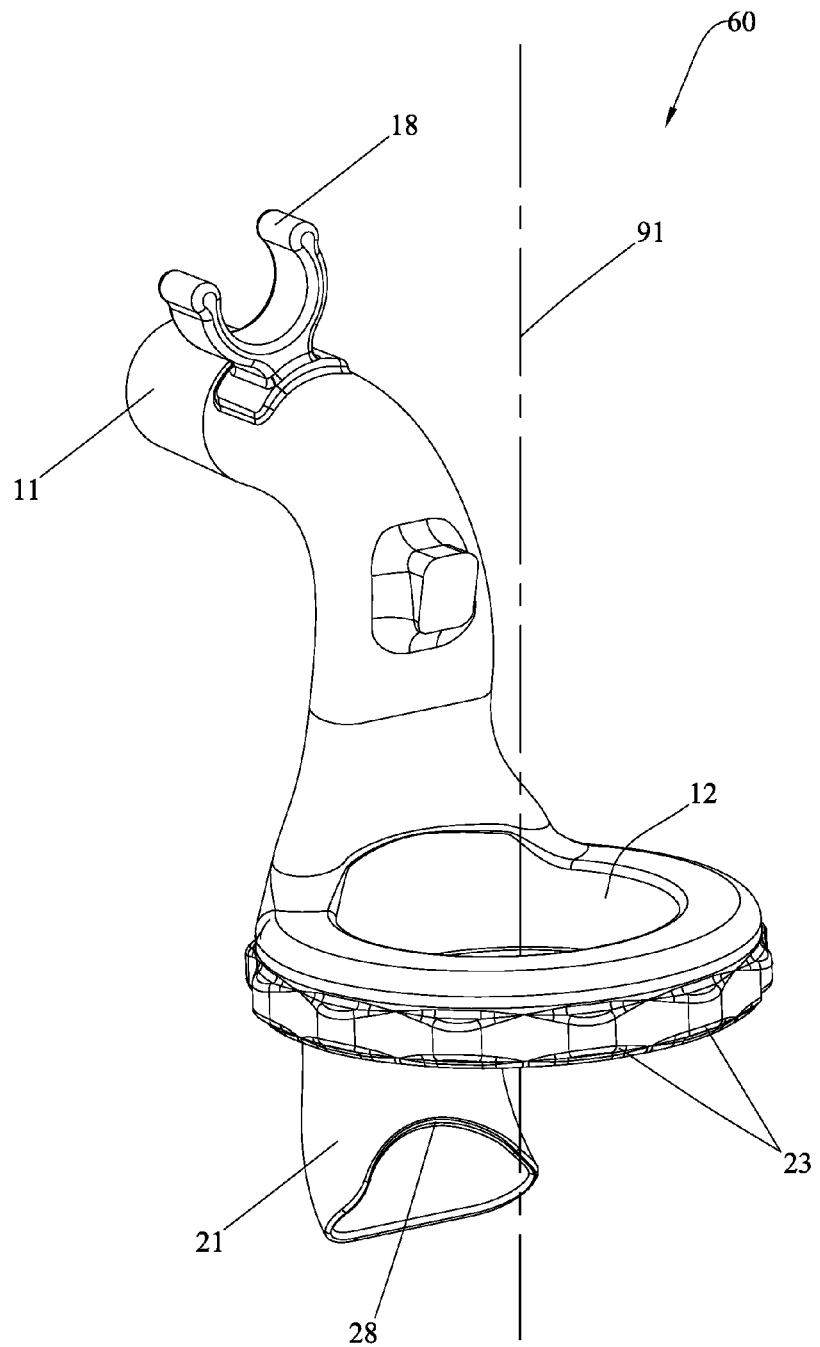
FIG. 2 is an isometric view of the first embodiment.
Figure 3:
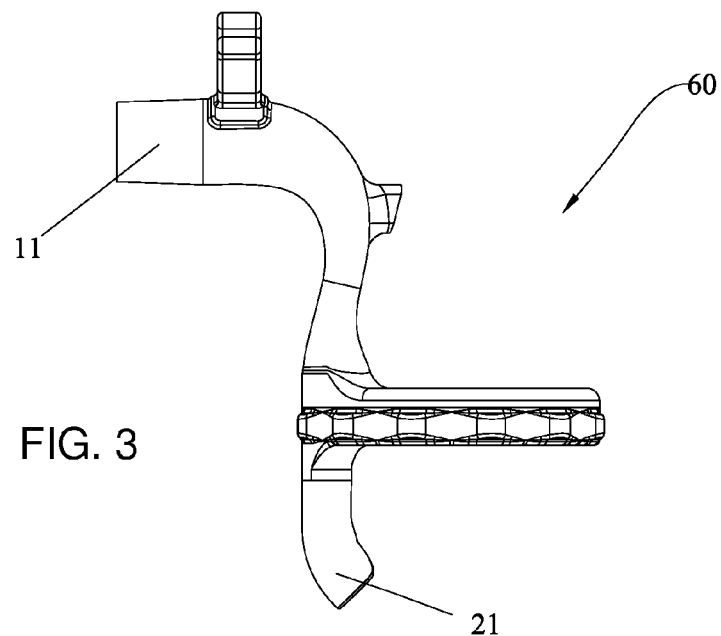
FIG. 3 is a side view of the first embodiment.

The joint or connection formed between adapter parts 10 and 20 allows sliding relative rotation about axis 91. In one embodiment, the outer circumference of second ring-shaped portion 27 is lined with multiple finger grips 23. Finger grips 23 give increased friction when a user wishes to rotate second adapter part 20 relative to first adapter part 10 about axis 91. Generally toroidal cavity 25 communicates with downward extending inlet 21. Tubular outlet 11 is thus in fluid communication with inlet 21 through toroidal cavity 25. By rotating part 20 relative to part 10, the position of inlet 21 is changed. As shown in FIG. 2, inlet 21 extends from ring-shaped portion 27 both downwards and towards axis 91. Inlet 21 has a generally elliptical cross section in this embodiment. The outer rim of inlet 21 also has curved upper lip 28.

Figure 4:
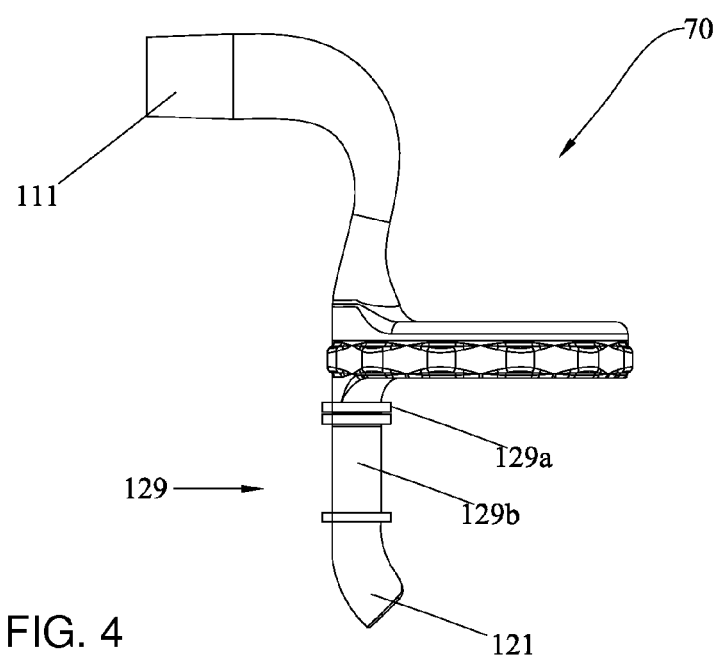
FIG. 4 is a side view of a second embodiment.

FIG. 4 shows a side view of embodiment 70 which contains a telescopic inlet portion 129. Inlet portion 129 is made up of tubular parts 129a and 129b. Tubular part 129a has a tube diameter slightly smaller than tubular part 129b, which has a tube diameter slightly smaller than the tubular body diameter of inlet 121. This allows tubular part 129a to slidably engage tubular part 129b and similarly tubular part 129b to slidably engage inlet 121. This enables the inlet (121) to be extended downwards, while allowing fluid communication to be maintained between generally toroidal cavity and inlet 121.

The operation of embodiment 60 together with an example laser apparatus 30 is shown in FIG. 5. Laser apparatus 30 contains conical portion 35, at the bottom of which a horizontally mounted lens is arranged which directs a laser beam downwards along axis 91. When attaching embodiment 60 to laser apparatus 30, embodiment 60 is lifted upwards such that inner surface 12 compressively engages the lens' outer cylindrical surface. Tubular outlet 11 is connected to a vacuum tube, and the vacuum is turned on causing air to flow into inlet 21. As laser apparatus 30 is used in medical procedures, smoke cone 44 forms. Smoke is rapidly drawn into inlet 21, where it is either filtered or vented outside by the vacuum.

Figure 6:
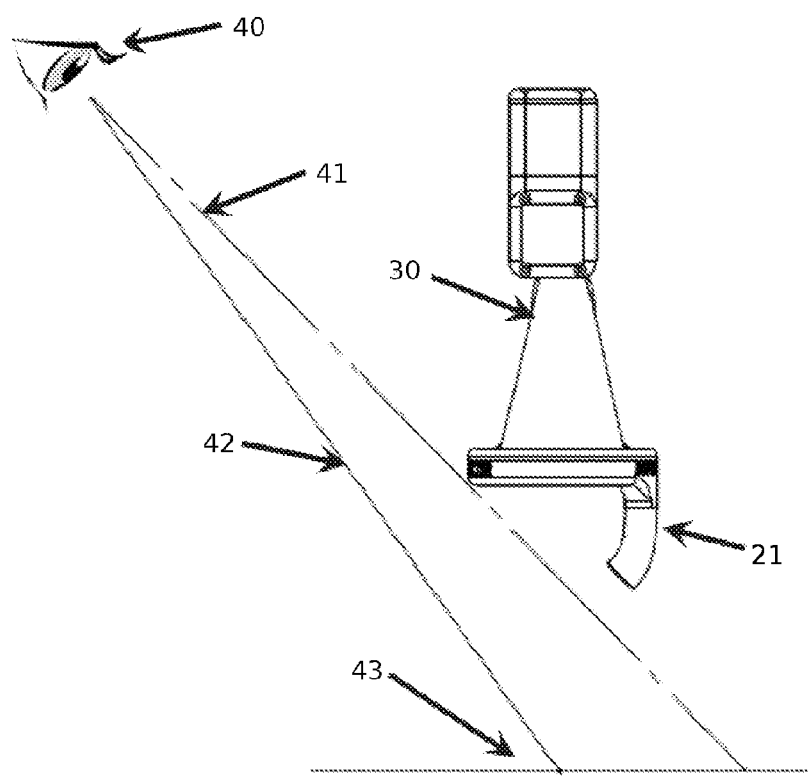
FIG. 6 is a side view of the first embodiment attached to a laser apparatus showing a user's field of view.

As shown in FIG. 6, user 40 may adjust the position of inlet 21 by rotating second adapter part 20 relative to the first adapter part (10). This will allow user 40 to ensure that his/her field of view 41-42 is not obstructed by the inlet (21).

Figure 7:
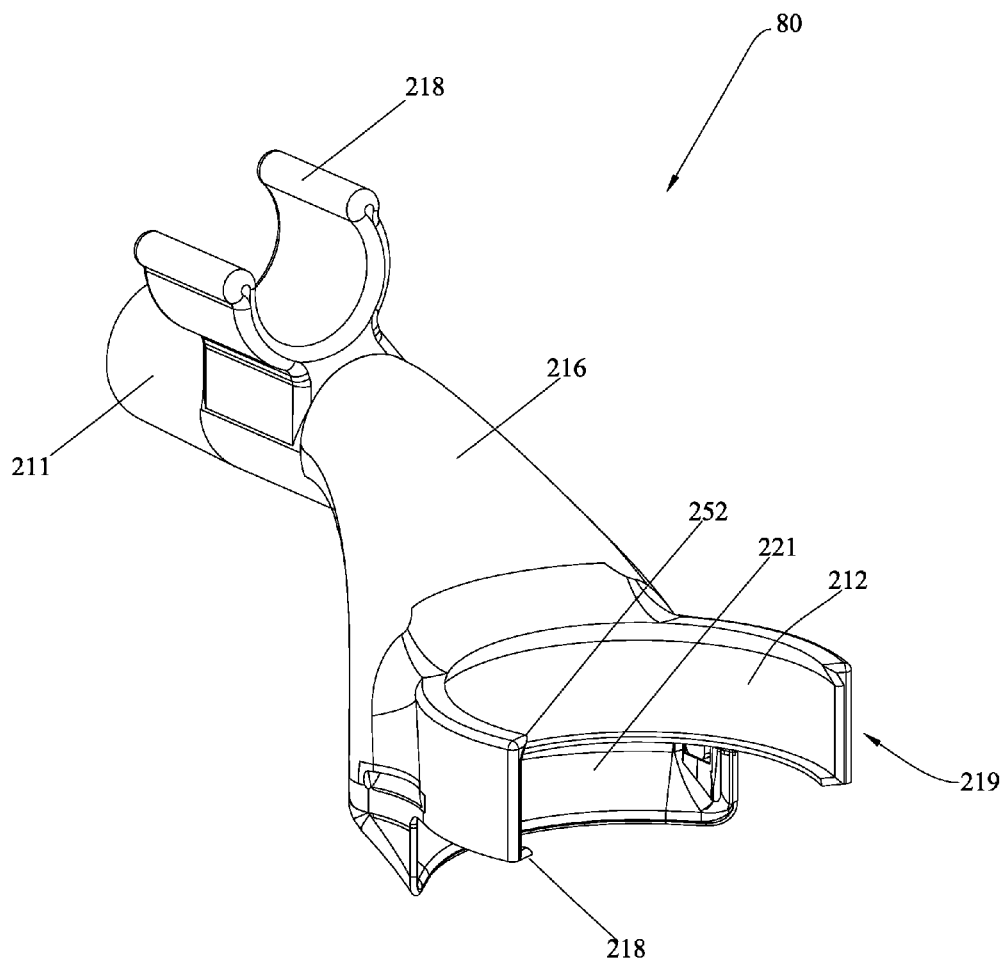
FIG. 7 is an isometric view of a third embodiment.
Figure 9:
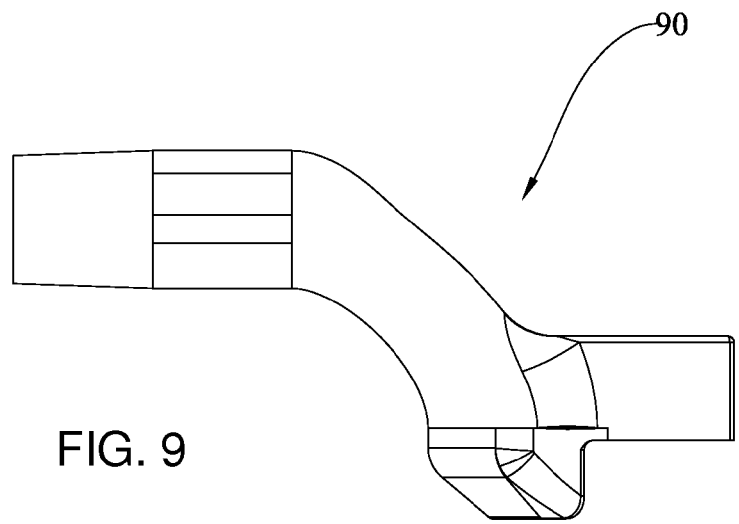
FIG. 9 is a side view of a fourth embodiment.
Figure 8:
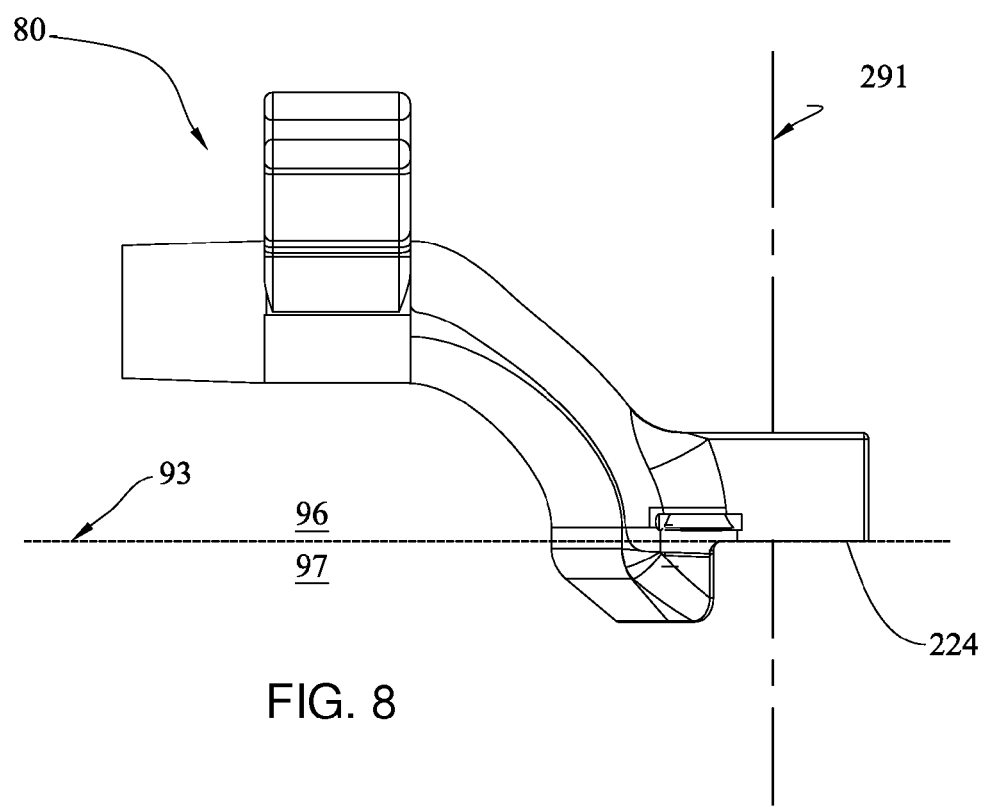
FIG. 8 is a side view of the third embodiment.

Additional embodiment 80 is shown in FIGS. 7 and 8. Similar to embodiment 60, embodiment 80 has horizontally oriented tubular outlet 211 upon which clip 218 is mounted. Tubular outlet 211 connects to hollow body 216. Hollow body 216 has a generally conical shape oriented at an angle, with a diameter that increases downwards along the body. Hollow body 216 connects to inlet 221. Inlet 221 faces towards axis 291 and has a generally rectangular cross section. Horizontally oriented semi-cylindrical portion 219 is attached near the base of hollow body 216, just above inlet 221. Semi-cylindrical portion 219 has vertical inner surface 212, which is bounded by upper ridge 252 and lower ridge 253. The dimensions of inner surface 212 are configured such that inner surface 212 compressively engages an outer surface of laser apparatus 30.

Figure 10:
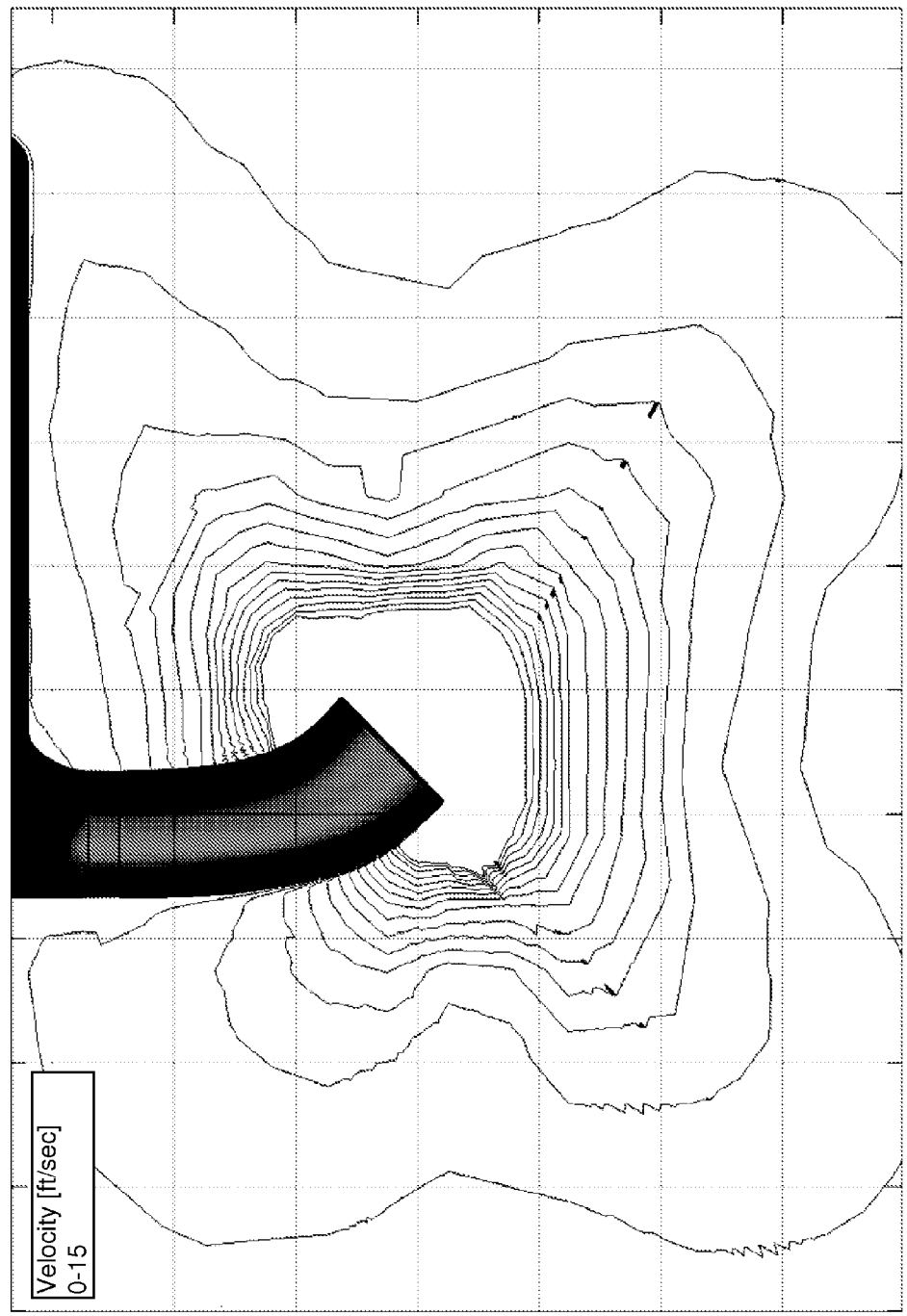
FIG. 10 is an velocity flow graph of a simulation of airflow around the inlet of the first embodiment.

FIG. 10 shows an example flow analysis of the air speed distribution in close proximity of intake 21 nozzle for embodiment 60. The flow speed resolution is 1 ft/min with the outermost line showing the border between 0-0.99 ft/min and 1+ ft/min. The flow volume rate for the intake in this simulation is 30 CFM.

Ring-shaped portions 17 and 19 and semi-cylindrical portion 219 may be adapted to fit the sizes and shapes of various laser devices and lenses (ring-shaped or otherwise). The invention may be made of plastic, metal or other material in order to make the device autoclavable. Other additional materials known to those skilled in the art may also be used. The invention may be manufactured by, but not limited to, injection molding and thermoform. The adapter may be configured such that air, smoke, and liquid may flow in through the inlet. The invention contemplates changes to the dimensions of the disclosed embodiments for attachment to various laser devices that include, but are not limited to: Alma, Reliant (Solta Med), Sciton, Aesculight, Eclipse Med and Lumenis lasers. Additionally, different nozzle geometries may be used to accommodate various laser bodies and laser beam trajectories may be used. Similarly, variations may be made in the attachment mechanisms to accommodate various laser geometries. An embodiment may have multiple intake nozzles. Lights may be added to the disclosed embodiments, extending from or attached to the apparatus to improve the view around surgical area since light is generally obstructed by the user and the laser apparatus itself. Additionally, it is contemplated that a magnification glass may be mounted on the apparatus to improve visibility for the user. Further, a cold air exhaust port may be added for cooling the tissue being treated.

The present invention contemplates that many changes and modifications may be made to the disclosed embodiments. Therefore, while the presently-preferred form of the invention has been shown and described, those persons skilled in this art will readily appreciate that various additional changes and modifications may be made without departing from the spirit of the invention, as defined and differentiated by the claims.

What is claimed is:

1. A smoke capture adapter, comprising:
   a first adapter part comprising:
      a first generally ring-shaped portion with a first cylindrical inner surface for securely engaging a laser apparatus having a beam propagation axis, said first generally ring-shaped portion being oriented such that said beam propagation axis passes through a region bound by said first generally ring-shaped portion; and
      a tubular outlet extending from said first generally ring-shaped portion arranged for communication with a vacuum tube;
   a second adapter part rotatably connected to said first adapter part and arranged to rotate generally about said beam propagation axis, said adapter second part comprising:
      a second generally ring-shaped portion adjacent said first generally ring-shaped portion, said first and second generally ring-shaped portions defining a generally toroidal cavity; and
      an inlet in fluid communication with said generally toroidal cavity;
   said tubular outlet and said inlet in fluid communication through said cavity;
   whereby the position of said inlet relative to said first adapter part may be adjusted by rotating said second adapter part relative to said first adapter part.

2. The smoke capture adapter of claim 1, wherein said first cylindrical inner surface is configured to compressively engage said laser apparatus.

3. The smoke capture adapter of claim 2, wherein said laser apparatus comprises an outer cylindrical surface of a lens body, and said first cylindrical inner surface is configured to compressively engage said outer cylindrical surface.

4. The smoke capture adapter of claim 1, wherein said second adapter part is configured and arranged to rotate 360 degrees relative said first adapter part.

5. The smoke capture adapter of claim 1, wherein said inlet is telescopic.

6. The smoke capture adapter of claim 1, wherein said second adapter part further comprises finger grips on an outer circumference of said second adapter part.

7. The smoke capture adapter of claim 1, wherein said cylindrical inner surface comprises a clip on said tubular outlet configured for connection to said laser apparatus.

8. The adapter of claim 1, wherein said inlet tapers outwardly from said generally toroidal cavity.

9. A smoke capture adapter for use with a laser apparatus having a laser propagation path, comprising:
   an inlet configured for orientation towards said laser propagation path;
   a tubular outlet in fluid communication with said inlet and oriented away from said laser propagation path;
   compressive attachment means for connecting said smoke capture adapter to said laser apparatus;
   adjustment means for adjusting the rotational position of said inlet relative to said outlet about said laser propagation path.

10. The adapter of claim 9, wherein said adjustment means comprises a joint configured to rotate generally about said laser propagation path.

11. The adapter of claim 9, wherein said compressive attachment means comprises a semi-cylindrical surface configured to compressively engage a cylindrical surface of said laser apparatus.

12. The adapter of claim 9, wherein said inlet is telescopic.

* * * * *